US00PP32494P2

(12) United States Plant Patent
Molnar et al.

(10) Patent No.: US PP32,494 P2
(45) Date of Patent: Nov. 24, 2020

(54) ***CORYLUS* PLANT NAMED 'SOMERSET'**

(50) Latin Name: ***Corylus avellana* cultivar**
Varietal Denomination: Somerset

(71) Applicant: RUTGERS, THE STATE UNIVERSITY OF NEW JERSEY, New Brunswick, NJ (US)

(72) Inventors: Thomas J. Molnar, East Brunswick, NJ (US); Shawn A. Mehlenbacher, Corvallis, OR (US); John M. Capik, Somerset, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 16/602,128

(22) Filed: Aug. 12, 2019

(51) Int. Cl.
*A01H 5/08* (2018.01)
*A01H 6/00* (2018.01)

(52) U.S. Cl.
USPC ..... Plt./152
CPC ..... *A01H 6/00* (2018.05)

(58) Field of Classification Search
USPC ..... Plt./152
CPC ..... A01H 5/0825
See application file for complete search history.

(56) References Cited

PUBLICATIONS http://thescalepit.com/ContentHN/Hazel%20Dormancy%20and%20Pollination.pdf; Apr. 8, 2019; 9 pages.*

* cited by examiner

*Primary Examiner* — Kent L Bell
(74) *Attorney, Agent, or Firm* — Patrick J. Daugherty; Daugherty & Del Zoppo Co., LPA

(57) ABSTRACT

A new and distinct *Corylus avellana* plant named 'Somerset' characterized by a semi-vigorous, compact growth habit, the production of nuts with thin shells and globular kernels that fall free of the husk at maturity, and resistance to eastern filbert blight caused by the fungus *Anisogramma anomala* (Peck) E. Müller.

5 Drawing Sheets

Latin name: *Corylus avellana* cultivar.
Variety denomination: 'Somerset'.

BACKGROUND OF THE INVENTION

The present invention relates to a new and distinct cultivar of *Corylus* plant, botanically known as *Corylus avellana*, the designation 'Somerset', or as 'Somerset' Hazelnut (CRXR04P43 Rutgers 5), and hereinafter referred to by the name 'Somerset'. The new *Corylus* resulted from a controlled cross of the female parent OSU 665.123 x 'Ratoli' (male parent). Hybrid seeds resulting from the cross were harvested in August 2000. They were provided a period of moist chilling, subsequently germinated, and the seedlings were grown in the greenhouse during the summer of 2001. The seedling trees were maintained through the year in containers and were provided chilling during the winter of 2001/2002 in a cool greenhouse. Finally, a total of 106 seedling trees were planted in a research field in Cream Ridge, N.J., in October 2002. 'Somerset' was discovered and selected as a single plant within that progeny of the stated cross-pollination. It was originally assigned the designation CRXR04P43, which indicates the field, row, and tree location of the original seedling.

The female parent OSU 665.123 is an unreleased seedling. The male parent 'Ratoli' is a minor cultivar from Tarragona, Spain (Tasias-Valls, 1975), found to carry a single dominant resistance allele that confers resistance to eastern filbert blight (EFB) caused by the fungus *Anisogramma anomala* (Peck) E. Müller.

'Somerset' was asexually reproduced by rooted suckers and whip grafting in 2008 through 2015 in Cream Ridge, East Brunswick, and New Brunswick, N.J. The unique features of this new *Corylus* are stable and reproduced true-to-type in successive generations of asexual reproduction.

BRIEF SUMMARY OF THE INVENTION

The following traits have been observed and are determined to be the unique characteristics of 'Somerset'. These characteristics in combination distinguish 'Somerset' as a distinct cultivar:

Semi-vigorous and compact plant habit.

Green to dark-green color of developing and fully expanded leaves during the spring and summer.

High level of resistance to eastern filbert blight (EFB) caused by the fungus *Anisogramma anomala* (Peck) E. Müller. The source of this resistance is from 'Ratoli' (unpatented, Lunde et al., 2000; Sathuvalli et al., 2011), which differs from the single dominant allele conferred from 'Gasaway' (unpatented, Mehlenbacher et al., 1991), which protects *Corylus avellana* 'McDonald' (U.S. Pat. No. 28,200P3, Mehlenbacher et al., 2016), 'Wepster' (U.S. Pat. No. 27,141P3, Mehlenbacher et al., 2014), 'Dorris' (U.S. Pat. No. 25,022P3, Mehlenbacher et al., 2014), 'Jefferson' (unpatented, Mehlenbacher et al., 2011a), 'Yamhill' (unpatented, Mehlenbacher et al., 2009), and several other *Corylus avellana* cultivars and pollenizers.

Expression of incompatibility alleles S3 and S10 in the styles.

Comparisons in several replicated plantings in Cream Ridge and East Brunswick, N.J., show that plants of 'Somerset' differed from plants of the *Corylus avellana* cultivar 'Barcelona' (unpatented), 'Tonda di Giffoni' (unpatented), 'Yamhill', 'Jefferson', and other cultivars and selections of *Corylus avellana* known to the Inventors, primarily in their response to EFB present in New Jersey, a region where the pathogen is native and highly genetically diverse (Muehlbauer et al., 2019). They also differed in S-alleles, nut size, kernel percentage (ratio of kernel weight to nut weight), frequency of defects (blank nuts, moldy kernels, twin kernels, etc.), time of pollen shed, and length of the husk or involucre. 'Somerset' is immediately distinguished from its parents in several ways. 'Somerset' expresses incompatibility alleles (S-alleles) S3 and S10 in its stigmas whereas 'Ratoli' expresses S2 and S10 and OSU 665.123 expresses S2 and S3. Furthermore, 'Somerset' has been shown to be resistant to eastern filbert blight caused by *Anisogramma anomala* and has never displayed any signs or symptoms of disease, unlike its parent OSU 665.123 which is known to be susceptible to infection. 'Somerset' also exhibits differing flowering phenology than 'Ratoli', as both male and female flowers emerge consistently later than 'Ratoli' as shown in FIG. 4.

For example:

Eastern filbert blight response in New Jersey: In a multi-year trial in East Brunswick, N.J., 'Somerset' showed no eastern filbert blight compared to the proportion of EFB-diseased wood across the canopy calculated to be 20.4% for 'Yamhill', 31.2% for 'Jefferson', 48.6% for 'Gasaway', and 67.0% for 'Barcelona'.

Pollen shed: 'Somerset' generally sheds pollen in East Brunswick, N.J., with 'Yamhill' and 'Santiam' (unpatented, Mehlenbacher et al., 2007), after 'Ratoli' (unpatented, minor cultivar from Tarragona, Spain), and prior to 'Jefferson' and 'Gasaway'. 'Somerset' =descriptor-5.

Husk Length: 'Somerset' is 1.25 times nut length, slightly shorter than 'Barcelona', while 'Wepster' is 2.0 times nut length.

'Somerset' produces kernels that are well-suited for the blanched kernel market for use in confections and baked goods. 'Somerset' combines resistance to eastern filbert blight (evaluated against *Anisogramma anomala* strains present in New Jersey, US) with globular nuts and kernels, a very high kernel percentage (very thin shell), and moderately good kernel blanching. The tree is semi-vigorous with a compact branching habit that produces a desirable orchard tree when pruned to a single stem.

Field observations in Cream Ridge and East Brunswick, N.J., and results from greenhouse-based inoculations performed in New Brunswick, N.J., indicate that 'Somerset' expresses resistance to eastern filbert blight (EFB) caused by the fungus *Anisogramma anomala*. The resistance is conferred by the single dominant allele from 'Ratoli', found on hazelnut linkage group 7 (Sathuvalli et al., 2011), which is unlike the cultivars currently grown in Oregon and Washington protected by the single dominant 'Gasaway' resistance allele found on linkage group 6 (Mehlenbacher et al., 2006). EFB is now present throughout the Willamette Valley or Oregon where 99% of the U.S. hazelnut crop is grown and is endemic to the eastern US and southern Canada, where it has been historically impossible to grow *Corylus avellana* commercially. 'Somerset' was selected in central New Jersey and is adapted to the climate present in this region. Pruning to remove cankers and fungicide applications are currently used to manage the disease in orchards of 'Barcelona' and other susceptible cultivars in the Pacific Northwestern US. 'Somerset' is suitable for planting in areas with high EFB disease pressure. It has shown resistance in the eastern US where the EFB fungus is native and genetically diverse (Muehlbauer et al., 2019).

BRIEF DESCRIPTION OF THE DRAWINGS

The figures include color photographic illustrations that illustrate the overall appearance of the new cultivar, showing the colors as true as it is reasonably possible to obtain in colored reproductions of this type. Foliage colors in the photographs may differ slightly from the color values cited in the detailed botanical description which accurately describe the colors of the new *Corylus*.

DETAILED BOTANICAL DESCRIPTION

Figure 1:
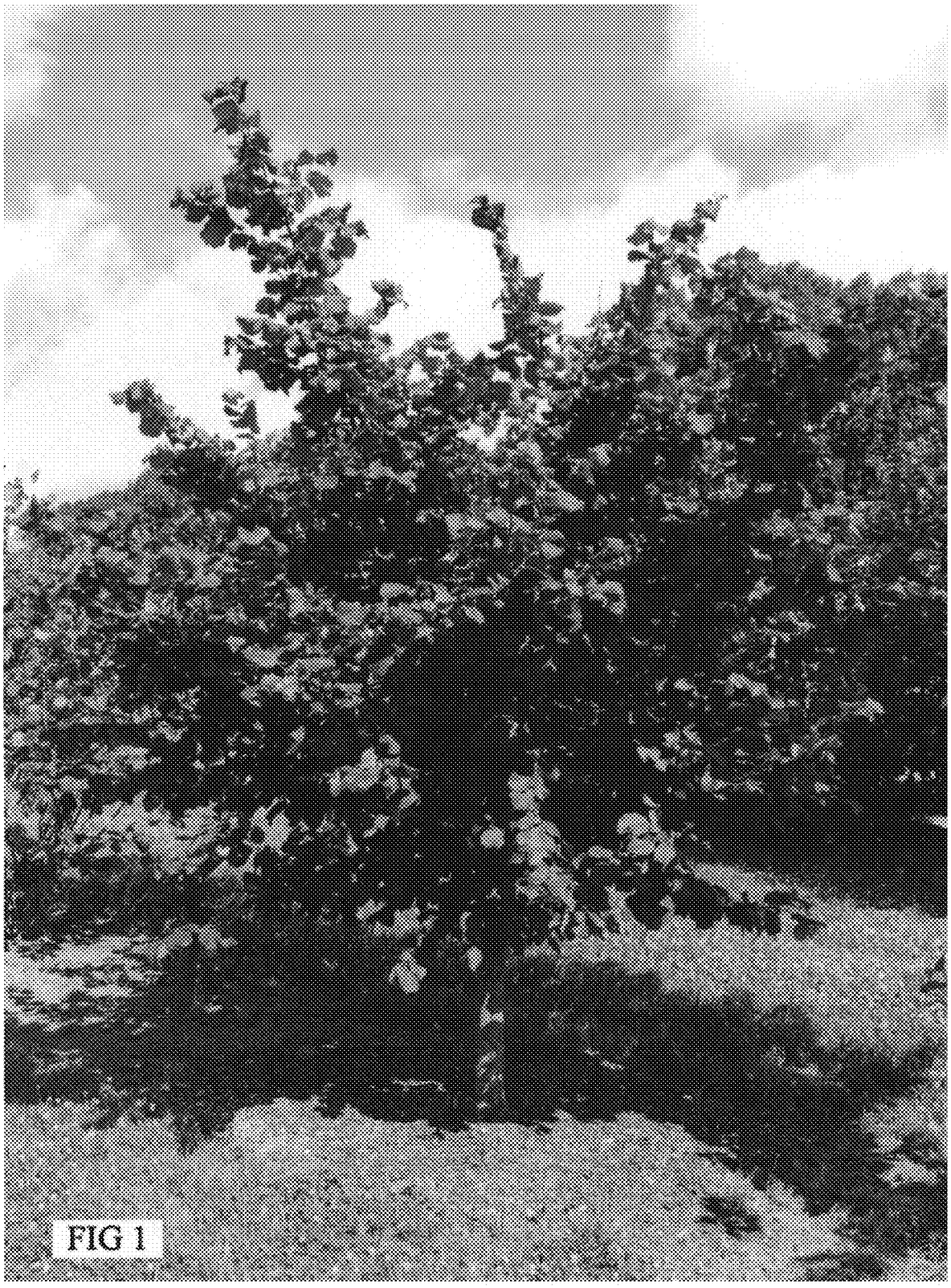
FIG. 1 is a color photographic illustration of a tree of the new cultivar 'Somerset' hazelnut in the eighth leaf pruned to a single trunk.

The cultivar 'Somerset' has not been observed under all possible environmental conditions. The phenotype may vary somewhat with variations in environment such as temperature and light intensity, without, however, any variance in genotype.

The aforementioned photographs and following observations and measurements describe plants grown in East Brunswick, N.J., under commercial practice outdoors in the field during the spring and summer. Plants used for the photographs and description were the original tree (15 years old) and those propagated by tie-off layerage and growing on their own roots (seven and eight years old).

Color references herein are made to The Royal Horticultural Society Colour Chart, 1966 Edition, except where general terms of ordinary dictionary significance are used. International Union for the Protection of New Varieties of Plants ("UPOV") descriptors are described in the Mar. 28, 1979, UPOV Hazelnut guidelines.

Botanical classification: *Corylus avellana* cultivar 'Somerset'.

Parentage: Female, or seed, parent is *Corylus avellana* OSU 665.123 (unpatented, unreleased seedling from Corvallis, Oreg. OSU 665.123 is the result of a cross of OSU 245.098 (unpatented, unreleased seedling) x 'Mortarella' (unpatented, Italian origin). OSU 245.098 is a cross of OSU 17.075 (unpatented, unreleased seedling) x 'Willamette' (unpatented, Mehlenbacher et al., 1991b). OSU 17.075 is the result of a cross of 'Barcelona' x 'Tombul Ghiaghli' (unpatented, Turkish origin). Male, or pollen, parent is *Corylus avellana* 'Ratoli' (unpatented, minor cultivar from Tarragona, Spain; Tasias-Valls, 1975).

'Ratoli' has been shown to transmit a dominant allele for resistance to EFB, which has been mapped to a different linkage group than the allele from 'Gasaway'. The 'Ratoli' allele that protects 'Somerset' has been shown to provide resistance in the presence of multiple isolates of the EFB fungus *Anisogramma anomala* including those present in New Jersey (Lunde et al., 2000; Molnar et al., 2010, 2019; Sathuvalli et al., 2011).

Incompatibility alleles: 'Somerset' has incompatibility alleles S3 and S10. Female parent OSU 665.123 has alleles S2 and S3. The male parent 'Ratoli' has alleles S2 and S10. 'Sacajawea' has alleles S1 and S22. 'Tonda di Giffoni' has the alleles S2 and S23, 'Tonda Pacifica' (U.S. Pat. No. 22,715, Mehlenbacher et al., 2011b) and 'Wepster' have alleles S1 and S2, and 'McDonald' has alleles S2 and S15.

Propagation (type rooted suckers):

*Time to initiate roots*.—About 30 days at 20° C.

*Time to produce a rooted young plant*.—About six months at 22° C.

*Root description*.—Fine to thick; freely branching; creamy white in color.

Propagation (type whip grafting):

*Time to budbreak on the scions*.—About 14 days at 25° C.

*Time to produce a grafted plant*.—About six months at 25° C.

Plant description:

*General appearance*.—Natural habit is perennial shrub, but in commercial orchards, is a single trunk tree. Rounded, compact habit.

*Growth and branching habit*.—Freely branching; about 15 lateral branches develop per plant. Pinching, that is, removal of the terminal apices, enhances branching with lateral branches potentially forming at every node.

*Vigor*.—Moderate vigor growth habit.

*Size*.—Plant height is about 3.2 meters; plant diameter or spread is about 3.4 meters.

*Trunk*.—At 30 cm above the soil line, 7.5 cm in 2019. Texture is mostly smooth, glabrous.

*Trunk color*.—198A.

Lateral branch description:

*Length*.—About 16.4 cm; ranges from 12.0 cm to 27.0 cm.

*Diameter*.—About 4.1 mm; ranges from 3.0 mm to 5.0 mm.

*Internode length (at base)*.—About 0.5 cm.

*Internode length (at tip)*.—About 4.7 cm; ranges from 4.0 cm to 6.5 cm.

*Texture*.—Smooth, pubescent.

*Strength*.—Strong.

*Color, immature*.—144B.

*Color, mature*.—146D.

*Color of previous seasons branches*.—199B.

Foliage description:

*Arrangement*.—Alternate, simple.

*Length*.—About 9.9 cm; ranges from 8.0 cm to 12.0 cm.

*Width*.—About 8.6 cm; ranges from 7.0 cm to 10.0 cm.

*Shape*.—Oblong to ovate.

*Apex*.—Obtuse to acute.

*Base*.—Cordate.

*Margin*.—Serrate.

*Texture, upper and lower surfaces*.—Slightly pubescent.

*Venation pattern*.—Pinnate.

*Color*.—Developing foliage, upper surface 144A, lower surfaces, 144B.

*Fully expanded foliage, upper surface*.—Spring and summer, 136A; late summer and fall, 136A.

*Fully expanded foliage, lower surface*.—Spring and summer, 138B; late summer and fall, 138B.

*Venation, upper surface*.—Spring and summer, 144C; late summer and fall, 144C.

*Venation, lower surface*.—Spring and summer, 144C; late summer and fall, 144C.

Leaf bud description:

*Shape*.—Globular. Length: average 7.5 mm. Diameter: average 5.0 mm.

*Time of leaf budbreak*.—Medium, Descriptor-5. 'Somerset' budbreak is eleven days before 'Jefferson', one day after 'Yamhill', and three days before 'Santiam'.

*Color*.—145B.

Petiole description:

*Length*.—About 1.2 cm; ranges from 1.0 cm to 1.5 cm.

*Diameter*.—About 2.7 mm; ranges from 2.0 mm to 3.0 mm.

*Texture, upper and lower surfaces*.—Pubescent.

*Color*.—144C.

Flower description:

*Male inflorescences*.—Catkins.

*Color prior to elongation*.—176D.

*Catkin length*.—Average 30.0 mm; Catkin diameter: average 6.0 mm.

*Female inflorescence length at full maturity*.—Average 7.0 mm; style color: 47B.

*Time of female flowering*.—Early to medium, Descriptor-4.

*Time of female flowering compared to male flowering*.—Protogyny, Descriptor-1. Time of male flowering: early, Descriptor-3.

*Involucre constriction*.—Absent.

*Involucre length*.—1.25 times length of nut, Descriptor-7.

*Size of indentation*.—Weak, Descriptor-3.

*Strength of serration of indentation*.—Medium, Descriptor-5.

*Thickness of callus at base*.—Thin, Descriptor-3.

*Pubescence on husk*.—Absent, Descriptor-1.

*Density of hairiness of involucre*.—Weak, Descriptor-3.

*Jointing of bracts*.—On both sides, Descriptor-3.

Nut description:

*Length*.—Average 17.2 mm.

*Width*.—Average 17.7 mm.

*Depth*.—Average 19.3 mm.

*Nut shape*.—Globular, Descriptor-2.

*Nut shape index*.—(Width+Depth)/2*Length=1.08.

*Nut compression index*.—(Width/Depth)=0.92.

*Nut weight*.—Average 2.08 g.

*Kernel weight*.—Average 1.15 g.

*Kernel percentage*.—(Kernel weight/nut weight) average 54.5%

*Number of fruits per cluster*.—Three to four.

*Nutshell coloration*.—165B.

*Number of stripes on shell*.—Many, Descriptor-7.

*Shape of fruit apex*.—Flat, Descriptor-1.

*Prominence of fruit apex*.—Slightly prominent, Descriptor-3.

*Size of fruit pistil scar on shell*.—Large, Descriptor-7.

*Hairiness of top of fruit*.—Weak, Descriptor-3.

*Curvature of nut basal scar*.—Flat, Descriptor-2.

*Double kernels*.—Absent.

*Kernel shape*.—Globular, Descriptor-2.

*Shape of kernel in cross-section*.—Circular, Descriptor-2.

*Lateral groove in kernel*.—Present.

*Corkiness of pellicle of kernel*.—Smooth, Descriptor-1.

*Disease/pest resistance*.—Plants of 'Somerset' are resistant to EFB caused by the fungus *Anisogramma anomala* (Peck) E. Müller. It has been evaluated against the strains of the fungus present in New Jersey (Muehlbauer et al., 2019) and no signs or symptoms of the disease have been observed to date on the original clone or any asexually propagated plants. Plants have not been challenged against all strains of *Anisogramma anomala* present in North America, although 'Ratoli', the parent from which the resistance allele was derived, has been challenged in field trials and greenhouse inoculations with isolates from New Jersey, Oregon, Minnesota, Michigan, Massachusetts, New York, and Pennsylvania, and no EFB has been observed (Capik and Molnar, 2012; Lunde et al., 2000; Molnar et al., 2010). 'Somerset' has not been thoroughly evaluated for its tolerance of bud mites (*Phytoptus avellanae* Nal.); no bud mites were observed on the original tree or its propagules grown in Cream Ridge or East Brunswick, N.J. Further, no bacterial blight caused by *Xanthomonas campestris* pv. *corylina* was observed on the cultivar during the course of evaluations.

*Temperature tolerance*.—'Somerset' was selected in Cream Ridge, N.J., and is targeted for production in USDA Plant Hardiness Zones 6a to 7b. Plants of the new *Corylus avellana* have been observed to tolerate temperatures from −21 to 38° C.

COMPARATIVE DATA

Figure 4:
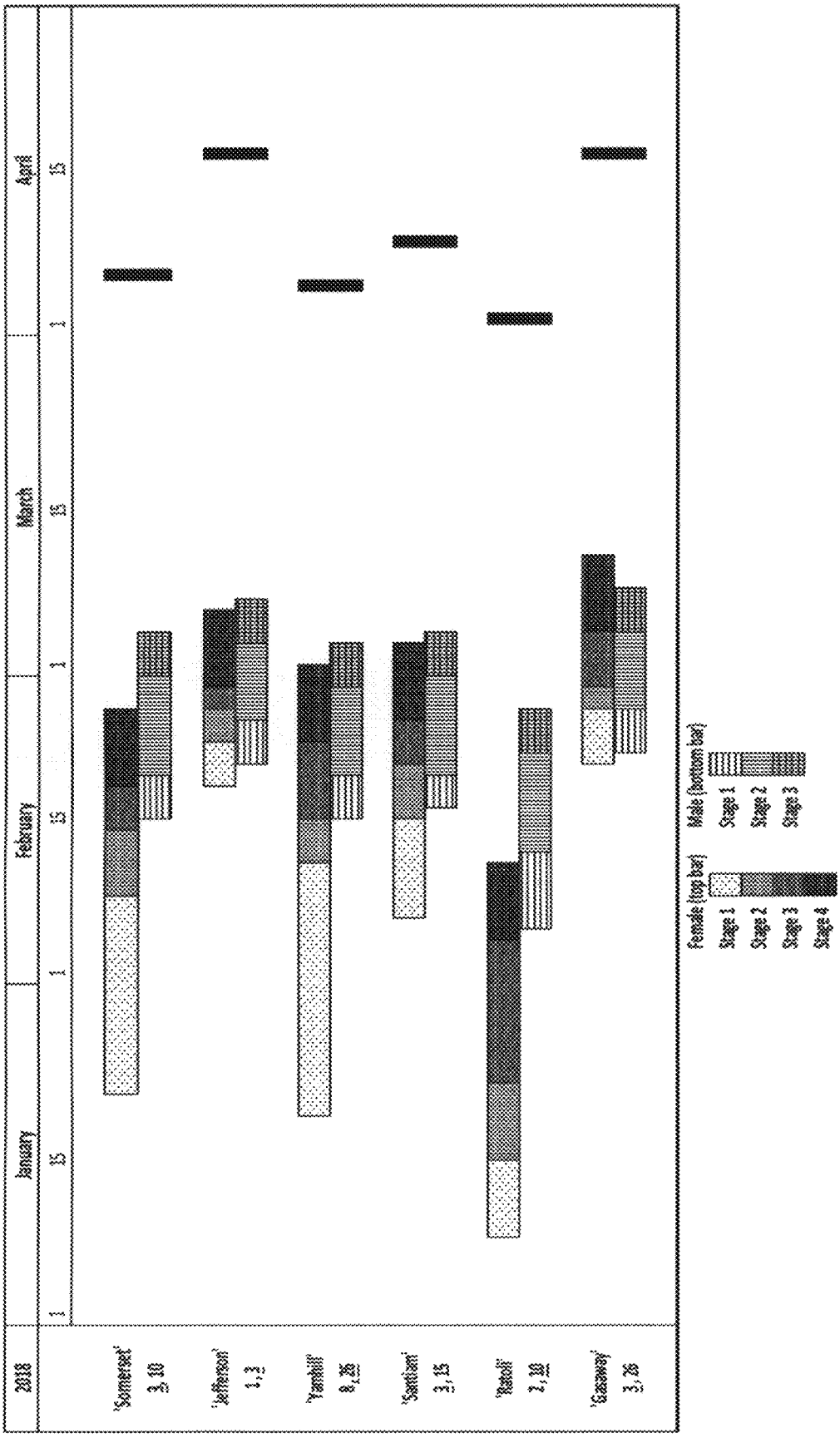
FIG. 4 is a phenology chart illustration that shows times of female receptivity, pollen shed, and vegetative budbreak of 'Somerset' and other hazelnut cultivars.

FIG. 4 presents a phenology chart showing time of female receptivity, pollen shed, and vegetative budbreak of 'Somerset' and other hazelnut cultivars grown in East Brunswick, N.J. over a time period from January to April of 2018. For each of the different indicated varieties ('Somerset', 'Jefferson', 'Yamhill', 'Santiam', 'Ratoli' and 'Gasaway') upper and lower bar graph pairings are provided in alignment with their respective varietal indicators, wherein the upper (top) bar graph of each pairing represents pistillate (female) flower development as it progresses over time through each of four stages represented by the crosshatchings key at the bottom of the chart; and the lower (bottom) bar graph of each pairing represents staminate (male) flower development as it progresses over time through each of three stages represented by different crosshatchings defined by another key at the bottom of the chart. The different respective stages correspond to the stages of development as defined and described in "Flowering phenology of eastern filbert blight-resistant accessions in New Jersey," Capik, J. M. and T. J. Molnar, HortTechnology 24:196-208, 2014 (hereinafter sometimes "Capik and Molnar (2014)"). Stage 1 of vegetative bud development for each of the varieties is represented by the solid black rectangles aligned with the varietal indicators.

Figure 5:
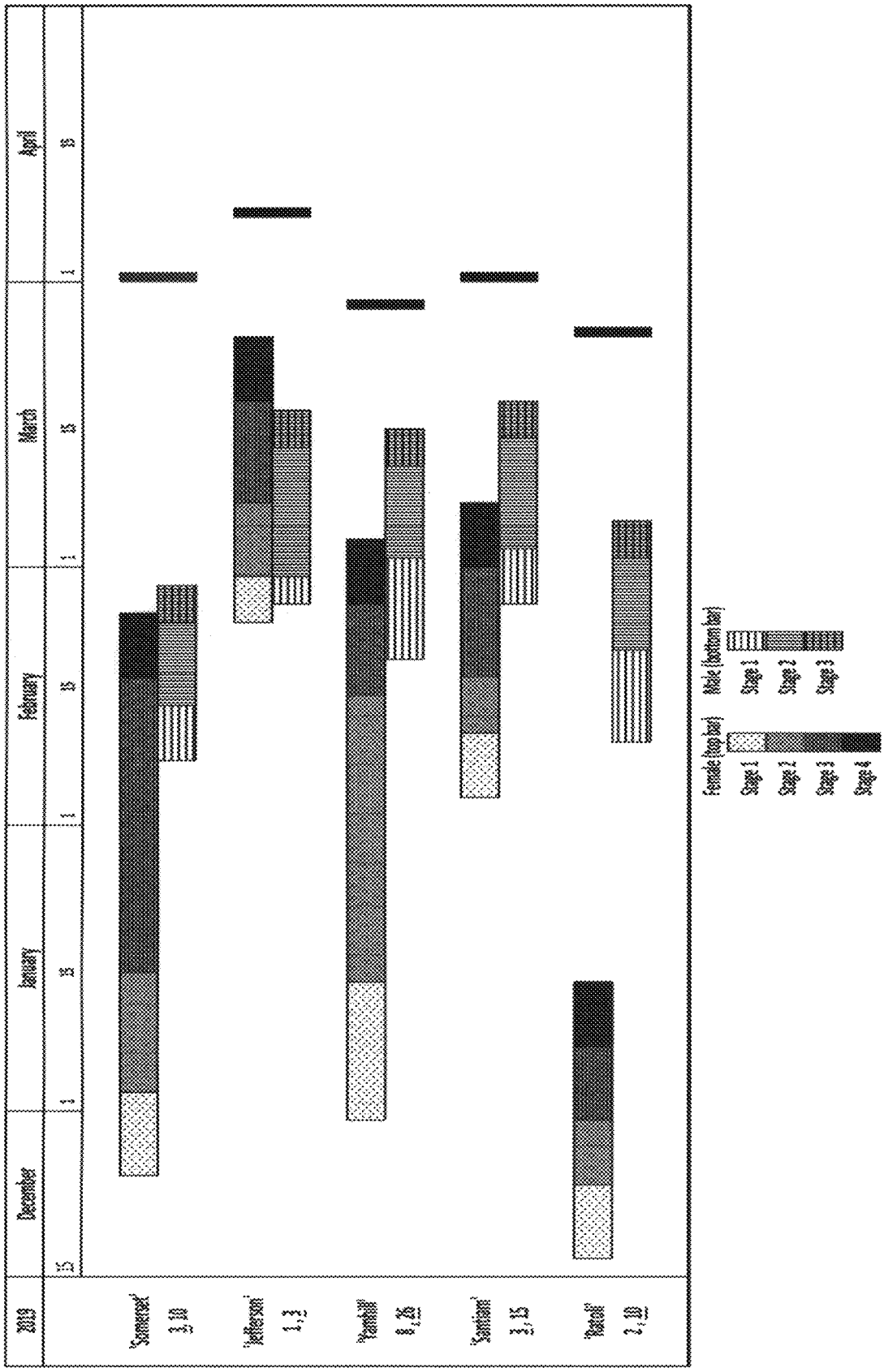
FIG. 5 is another phenology chart illustration that shows times of female receptivity, pollen shed, and vegetative budbreak of 'Somerset' and other hazelnut cultivars.

FIG. 5 presents a phenology chart showing time of female receptivity, pollen shed, and vegetative budbreak of 'Somerset' and other hazelnut cultivars grown in East Brunswick, N.J., from December 2018 to April 2019. For each of the different indicated varieties ('Somerset', 'Jefferson', 'Yamhill', 'Santiam', and 'Ratoli') upper and lower bar graph pairings are provided in alignment with their respective varietal indicators, wherein the upper (top) bar graph of each pairing represents pistillate (female) flower development as it progresses over time through each of the four Capik and Molnar (2014) stages represented by the crosshatchings key at the bottom of the chart; and the lower (bottom) bar graph of each pairing represents staminate (male) flower development as it progresses over time through each of three respective Capik and Molnar (2014) stages represented by crosshatchings defined by another key at the bottom of the chart. Stage 1 of vegetative bud development for each of the varieties is represented by the solid black rectangles aligned with the varietal indicators.

*Disease resistance*.—'Somerset' differs from existing *Corylus avellana* cultivars based on its source and type of resistance to eastern filbert blight (EFB) caused by *Anisogramma anomala*. Commercial cultivars previously widely grown in Oregon including 'Barcelona' (unpatented), 'Ennis' (unpatented), 'Daviana' (unpatented), 'Butler' (unpatented), etc. are highly susceptible to EFB and cannot be grown in the eastern US without copious applications of chemical fungicides and heavy pruning to remove infected wood. Tree death can occur in the eastern US within 5 years of exposure to the systemic fungus. The more recently developed cultivars 'Santiam', 'Yamhill', 'Jefferson', 'Dorris', 'Wepster', and 'McDonald' and their associated pollenizers are protected from EFB by a single resistance gene conferred from *Corylus avellana* 'Gasaway'. This gene provides a high level of resistance in Oregon and Washington where the diversity of the fungus is limited (Muehlbauer et al., 2019), but does not provide a similar level of protection from disease in the eastern US where the pathogen is endemic and genetically diverse (Capik and Molnar, 2012; Muehlbauer et al., 2018). 'Somerset' does not carry the single 'Gasaway' resistance allele. It carries the 'Ratoli' allele, which is a different gene on a different chromosome than 'Gasaway' (Sathuvalli et al., 2011). The allele from 'Ratoli' has been found to be very effective against the strains of *Anisogramma anomala* present in New Jersey and other locations (Molnar et al., 2010, 2019).

In a multi-year trial in East Brunswick, N.J., completed in winter 2018 and spanning more than 8 years of exposure to EFB, the average proportion of diseased wood (total length of EFB-diseased stems per tree divided by total length of shoot growth) for 'Somerset' was 0.0% (no EFB) compared to 20.4% for 'Yamhill' (unpatented, Mehlenbacher et al 2009), 31.2% for 'Jefferson' (unpatented, Mehlenbacher et al. 2011a), and 48.6% for 'Gasaway' (unpatented). Previous studies in New Jersey showed the proportion of diseased wood of 'Barcelona' to be 67.0%, 'Tonda di Giffoni' 39%, and 'Sacajawea' 21% (Capik and Molnar, 2012).

Differences were also observed in the number of cankers and average canker length for 'Somerset' in comparison to 'Yamhill', 'Jefferson', and 'Gasaway' in the study completed in 2018. 'Somerset' expressed no cankers. In contrast, 'Gasaway' exhibited an average of 93.0 cankers per tree with an average length of 130.8 cm, 'Jefferson' exhibited an average of 36.9 cankers per tree with an average length of 72.3 cm, and 'Yamhill' exhibited an average of 40.5 cankers per tree with an average length of 37.9 cm. As reported in Capik and Molnar (2012), and as a further point of comparison in regard to EFB response, 'Barcelona' exhibited an average of 20.4 cankers per tree with an average length of 61.9 cm, 'Tonda di Giffoni' exhibited an average of 39.0 cankers per tree with an average length of 24.5 cm, and 'Sacajawea' exhibited an average of 7.7 cankers per tree with an average length of 21.5 cm (Capik and Molnar, 2012).

Figure 3:
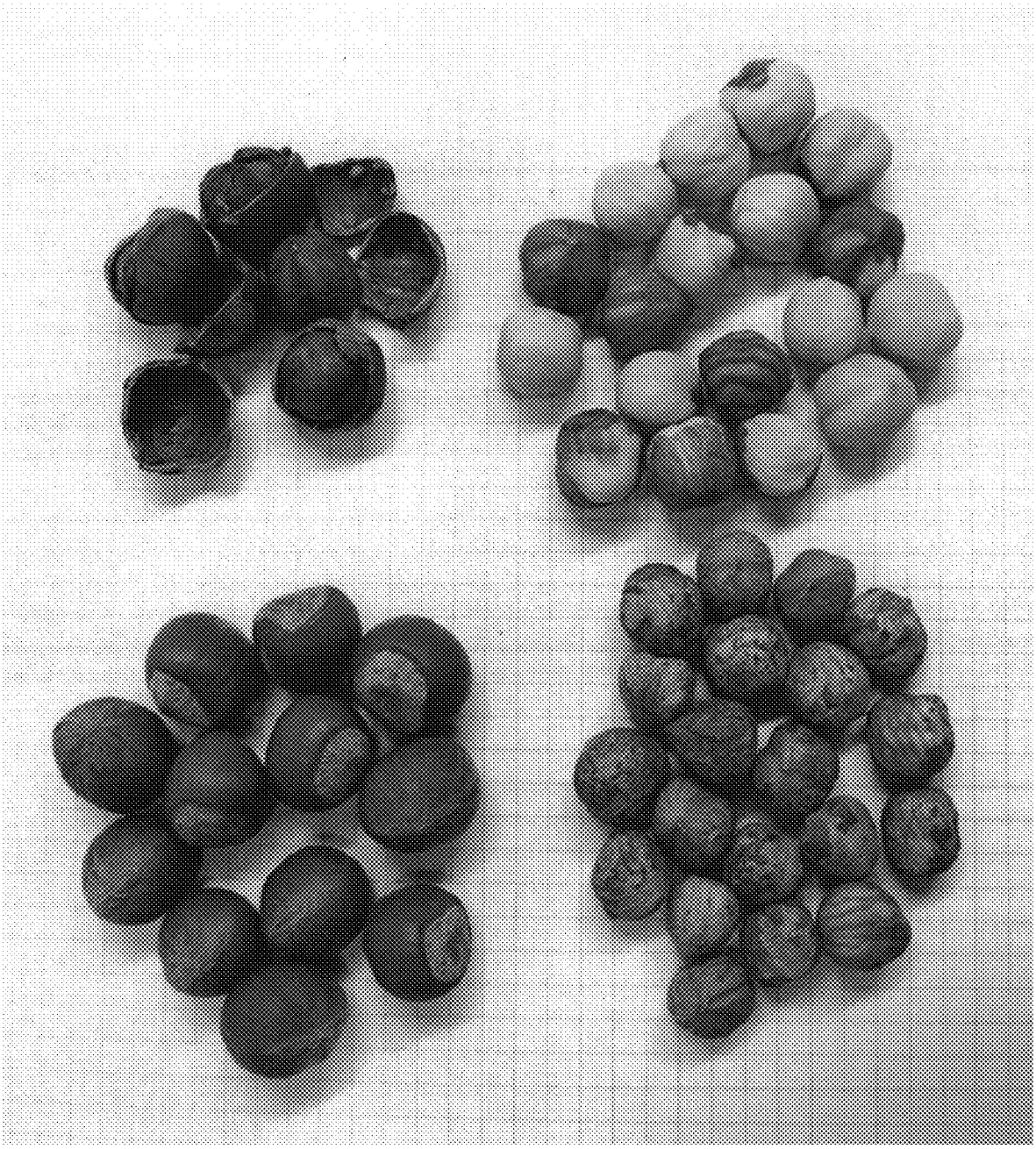
FIG. 3 is a color photographic illustration of nuts, cracked shells, raw kernels, and blanched kernels of hazelnuts 'Somerset'.

*Nut and kernel characteristics*.—'Somerset' hazelnut is targeted for the blanched kernel market and specifically for nut production in the eastern United States in USDA Plant Hardiness Zones 6a to 7b where most existing cultivars of *Corylus avellana* cannot be grown due to the impacts of EFB. The nut shape is globular. Kernels are globular. The average single nut weight over the past 6 years for 'Somerset' is 2.08 g, average single kernel weight is 1.15 g, with an average kernel to nut ratio of 54.5% (FIG. 3). 'Somerset' nuts and kernels are significantly smaller than those of 'Barcelona', 'Jefferson', and 'Sacajawea', and differ in kernel to nut ratio. For example, 'Barcelona' (as described in Mehlenbacher et al., 2008), had an average single nut weight of 3.85 grams, average single kernel weight of 1.66 grams, and an average kernel to nut ratio of 43.1%. 'Sacajawea' (as described in Mehlenbacher et al., 2008) had an average single nut weight of 2.79 grams, an average single kernel weight of 1.45 grams, and an average kernel to nut ratio of 52.1%. 'Jefferson' (as described in Mehlenbacher et al., 2011a) had an average single nut weight of 3.69 grams, an average single kernel weight of 1.66 grams, and an average kernel to nut ratio of 42.9%. 'Somerset' nuts and kernels are similar in size to 'Yamhill' and 'Wepster' and slightly smaller than 'McDonald' but differ from the three in several aspects especially ratio of kernel to nut ('Somerset' has very thin shells) but also pellicle removal after roasting. For example, 'Yamhill' (as described in Mehlenbacher et al., 2009), had an average single nut weight of 2.34 grams, an average single kernel weight of 1.13 grams, and an average kernel to nut ratio of 49.3%. 'Wepster' (as described in Mehlenbacher et al., 2014) had an average single nut weight of 2.39 grams, an average single kernel weight of 1.11 grams, and an average kernel to nut ratio of 46.6%. 'McDonald' (as described in Mehlenbacher et al., 2016) had an average single nut weight of 2.39 grams, an average single kernel weight of 1.21 grams, with an average kernel to nut ratio of 50.7%. Raw kernels of 'Somerset' have a light brown pellicle with a small amount of attached fiber (average rating was 2.0 on a scale of 1 [no fiber] to 4 [much fiber]). Pellicle removal after roasting at 150° C. for 15 min and rubbing is rated on a scale of 1 (complete pellicle removal) to 7 (no pellicle removal). Slightly more than half of the pellicle on 'Somerset' kernels is generally removed after roasting with an average rating of 3.5. 'Somerset' demonstrated better average pellicle removal than that reported in Oregon for 'Barcelona' (4.2 out of 7.0 as described in Mehlenbacher et al., 2008), 'Jefferson' (3.9 out of 7.0 as described in Mehlenbacher et al., 2011a), and 'Yamhill' (4.1 out of 7.0 as described in Mehlenbacher et al., 2011a). However, 'Somerset' has less pellicle removal after roasting than that described for 'Sacajawea' (2.9 out of 7.0 as described in Mehlenbacher et al., 2011), 'Dorris' (2.4 out of 7.0 as described in Mehlenbacher et al., 2013), and 'Tonda Pacific' described in Mehlenbacher et al., 2011). The average percentage of good kernels (kernels free of defects) were calculated for 'Somerset' and found to be 83.2%. There was on average 5.5% blank nuts, 1.5% moldy kernels, 6.3% nuts with shriveled kernels, 1.7% poorly filled, and 1.5% defective kernels attributed to defects from sucking insect damage, primarily Brown Marmorated Stink Bug (*Halyomorpha halys*, Stal, 1855). The percentage of good kernels for 'Somerset' were considerably higher than that reported for 'Barcelona' in multiple reports from Oregon (60.9% good kernels reported in Mehlenbacher et al. [2008] and 69.4% in Mehlenbacher et al. [2013]). The average percentage of good kernels for 'Somerset' grown in New Jersey are slightly lower than the range reported in Oregon for 'Yamhill', 'Jefferson', 'Dorris', and 'McDonald', however the percentage of moldy nuts was generally higher for these cultivars. There were only 0.2% twin kernels on average and no instances of black tips for 'Somerset'.

Figure 2:
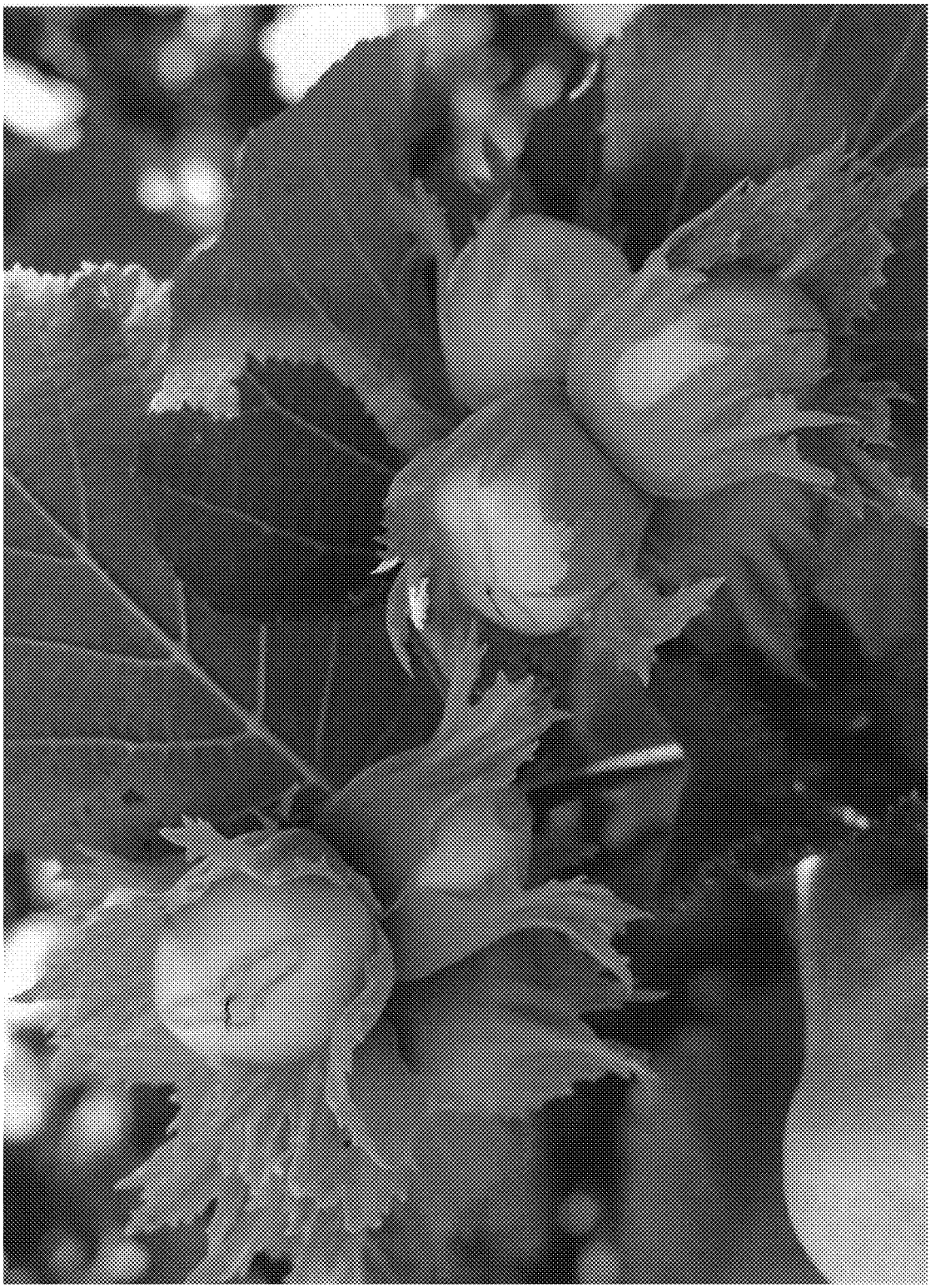
FIG. 2 is a color photographic illustration of nuts, husks, and leaves of 'Somerset' hazelnut.

*Nut maturity date*.—The nuts of 'Somerset' are typically borne in clusters of 3-4 in husks about 25-50% longer than the nuts. The husks are flared and slit down the side (FIG. 2), and open as they dry at maturity. About 90% of the nuts fall free of the husk at maturity (range 80-100%). The other 10% of the nuts come out of the husks as they move through the harvester. When mature, the shells are tan to light brown in color. Harvest date on average is around 10 days before 'Jefferson' when grown in East Brunswick, N.J., typically around the very last days of August or the first week of September.

*Incompatibility and pollinizers*.—The trees set a moderate to high amount of catkins that shed pollen in early season a few days prior to 'Yamhill'. Pollen has been collected and used in several controlled pollinations, and both quantity and viability appear to be good. 'Somerset' has incompatibility alleles S3 and S10 as determined by fluorescence microscopy. Both alleles are expressed in the female flowers and S3 is expressed by the pollen due to dominance. By convention, alleles expressed in the pollen are underlined. Time of pollen shed and female receptivity were recorded weekly from early December 2017 to late March 2019 (FIGS. 4-5). Climatic conditions vary each year and impact dates of bloom but not usually the order of progression of bloom among cultivars. Female inflorescences of 'Somerset' emerge in early season and are generally fully receptive around the first week of February in New Jersey. Pollinizer cultivars that shed compatible pollen in midseason and late midseason are recommended, with hybrid hazelnut seedlings (*Corylus americana* x *C. avellana*) planted as pollenizers in eastern and northern regions where cold temperatures and fluctuating climatic conditions can affect pollen production of *C. avellana*. Alternative orchard designs include also plantings different eastern filbert blight resistant cross-compatible cultivars in adjacent rows to augment pollen production. Flowering times will continue to be observed and pollinizer recommendations adjusted accordingly. Pollinizers must be selected that express a high level of EFB resistance to eliminate/reduce the need for fungicide control in the entire orchard.

*Pests and diseases*.—Based on results of field trials under high disease pressure and greenhouse inoculation trials, both performed in New Jersey, 'Somerset' expresses resistance to EFB. Resistance is derived from its parent 'Ratoli', which has been trialed in New Jersey since 2002 under high disease pressure with no signs or symptoms of EFB (Capik and Molnar, 2012; Molnar et al., 2019). Fungicide applications are not expected to be needed. Susceptibility to bacterial blight caused by *Xanthomonas campestris* pv. *corylina* has not been quantified, but the original seedling tree and clonal trees in the replicated trials were not affected. Susceptibility to big bud mite (primarily *Phytoptus avellanae* Nal.) has not been quantified, but the original tree and trees in the replicated trials were not affected.

*Propagation*.—Layers of 'Somerset' are vigorous and root well similar to standard cultivars of *Corylus avellana*.

REFERENCES

Capik, J. M. and T. J. Molnar. 2012. Assessment of host (*Corylus* sp.) resistance to eastern filbert blight in New Jersey. J. Amer. Soc. Hort. Sci. 137:157-172.

Capik, J. M. and T. J. Molnar. 2014. Flowering phenology of eastern filbert blight-resistant accessions in New Jersey. HortTechnology 24:196-208.

Lunde, C. F., S. A. Mehlenbacher, and D. C. Smith. 2000. Survey of hazelnut cultivars for response to eastern filbert blight inoculation. HortScience 35:729-731.

Mehlenbacher, S. A., M. M. Thompson, and H. R. Cameron. 1991a. Occurrence and inheritance of resistance to eastern filbert blight in 'Gasaway' hazelnut. HortScience 26:410-411.

Mehlenbacher, S. A., A. N. Miller, M. M. Thompson, H. B. Lagerstedt, and D. C. Smith. 1991b. 'Willamette' hazelnut. HortScience 26:1341-1342.

Mehlenbacher, S. A., A. N. Azarenko, D. C. Smith, and R. McCluskey. 2001. 'Clark' hazelnut. HortScience 36:995-996.

Mehlenbacher, S. A., R. N. Brown, E. R. Nouhra, T. Gökirmak, N. V. Bassil, and T. L. Kubisiak. 2006. A genetic linkage map for hazelnut (*Corylus avellana* L.) based on RAPD and SSR markers. Genome. 49:122-133.

Mehlenbacher, S. A., A. N. Azarenko, D. C. Smith, and R. McCluskey. 2007. 'Santiam' hazelnut. HortScience 42:715-717.

Mehlenbacher, S. A., D. C. Smith, and R. L. McCluskey. 2008. 'Sacajawea' hazelnut. HortScience 43:255 257.

Mehlenbacher, S. A., D. C. Smith, and R. L. McCluskey. 2009. 'Yamhill' hazelnut. HortScience 44:845-847.

Mehlenbacher, S. A., D. C. Smith, and R. L. McCluskey. 2011a. 'Jefferson' hazelnut. HortScience 46:662-664.

Mehlenbacher, S. A., D. C. Smith, R. L. McCluskey and M. M. Thompson. 2011b. 'Tonda Pacifica' hazelnut. Hort Science 46:505-508.

Mehlenbacher, S. A., D. C. Smith, and R. L. McCluskey. 2013. 'Dorris' hazelnut. HortScience 48:796-799.

Mehlenbacher, S. A., D. C. Smith, and R. L. McCluskey. 2014. 'Wepster' hazelnut. HortScience 49:346-349.

Mehlenbacher, S. A., D. C. Smith, and R. L. McCluskey. 2016. 'McDonald' hazelnut. HortScience 51:757-760.

Molnar, T. J., J. C. Goffreda, and C. R. Funk. 2010. Survey of *Corylus* resistance to *Anisogramma anomala* from different geographic regions. HortScience. 45:832-836.

Molnar, T. J., S. A. Mehlenbacher, P. Engel, and J. M. Capik. 2019. Multiple sources of eastern filbert blight resistance provide breeding utility in New Jersey. J. Amer. Pomological Soc. 73: 178-192.

Muehlbauer, M. F., Tobia J., Honig, J. A., Zhang N., Hillman, B. I., Morey Gold, K., and Molnar, T. J. 2019. Population differentiation within *Anisogramma anomala* in North America. Phytopathololgy. Published Online: 29 Apr. 2019 https://doi.org/10.1094/PHYTO-06-18-0209-R.

Sathuvalli, V. R., H. Chen, S. A. Mehlenbacher, and D. C. Smith. 2011a. DNA markers linked to eastern filbert blight resistance in 'Ratoli' hazelnut (*Corylus avellana* L.). Tree Genet. Genomes 7:337-345.

Tasias-Valls, J. 1975. El avellano en la provincial de Tarragona [in Spanish]. Excma. Diputacio´n Provincial de Tarragona, Fundacio´n Servicio Agropecuario Provincial, Tarragona, Spain.

What is claimed is:

1. A new and distinct cultivar of *Corylus* plant named 'Somerset', as illustrated and described.

* * * * *